United States Patent
Chapiro (10) Patent No.: US 10,179,219 B2
(45) Date of Patent: Jan. 15, 2019

(54) INTUBATION DEVICE WITH VARIABLE BACKFLOW PRESSURE

(71) Applicant: Daniel Marcos Chapiro, Palo Alto, CA (US)

(72) Inventor: Daniel Marcos Chapiro, Palo Alto, CA (US)

( * ) Notice: Subject to any disclaimer, the term of this patent is extended or adjusted under 35 U.S.C. 154(b) by 72 days.

(21) Appl. No.: 15/487,235

(22) Filed: Apr. 13, 2017

(65) Prior Publication Data

US 2018/0296782 A1    Oct. 18, 2018

(51) Int. Cl.
  *B01D 53/18*   (2006.01)
  *A61M 16/04*   (2006.01)
  *A61M 16/20*   (2006.01)
  *A61M 16/00*   (2006.01)

(52) U.S. Cl.
  CPC ...... *A61M 16/0459* (2014.02); *A61M 16/044* (2013.01); *A61M 16/0475* (2014.02); *A61M 16/208* (2013.01); *A61M 2016/003* (2013.01); *A61M 2016/0027* (2013.01); *A61M 2205/502* (2013.01); *A61M 2205/52* (2013.01)

(58) Field of Classification Search
  CPC ............ A61M 16/0459; A61M 16/044; A61M 16/208; A61M 16/0475; A61M 16/003; A61M 16/0027; A61M 2205/52; A61M 2205/502

See application file for complete search history.

(56) References Cited

U.S. PATENT DOCUMENTS

| | | | |
|---|---|---|---|
| 3,931,822 A | 1/1976 | Marici | |
| 4,020,849 A * | 5/1977 | Jackson | A61M 16/04 128/207.15 |
| 4,230,108 A | 10/1980 | Young | |
| 4,233,984 A | 11/1980 | Walling | |
| 4,235,239 A | 11/1980 | Elam | |
| 4,327,720 A | 5/1982 | Bronson | |
| 4,341,210 A | 7/1982 | Elam | |
| 4,423,725 A | 1/1984 | Baran | |
| 4,976,261 A | 12/1990 | Gluck | |
| 4,979,505 A | 12/1990 | Cox | |
| 5,033,466 A | 7/1991 | Weymuller | |
| 5,315,992 A | 5/1994 | Dalton | |
| 5,361,753 A | 11/1994 | Pothman | |
| 5,499,625 A | 3/1996 | Frass | |

(Continued)

FOREIGN PATENT DOCUMENTS

| | | |
|---|---|---|
| CA | 2141167 C | 7/2007 |
| WO | 2015013378 A1 | 1/2015 |

*Primary Examiner* — Gregory A Anderson
*Assistant Examiner* — Margaret M Luarca (57) ABSTRACT

Intubation devices, systems, and methods in which the risk of leakage of nasopharyngeal secretions, esophageal reflux, and blood is reduced, or eliminated, by means of a backflow pressure gradient that is independent of PEEP. Contemplated configurations include (a) a flexible tube for the controlled delivery of air and other gases to the lungs, (b) distal and proximal inflatable seals that can close the annular space surrounding the tube, (c) means to inflate the seals, and (d) means to deliver gas under pressure to the annular chamber in between the two seals. Further configurations further comprise a processor and sensors, and methods are provided for automated backflow of contaminated fluids.

14 Claims, 5 Drawing Sheets

(56) References Cited

U.S. PATENT DOCUMENTS

| | | | |
|---|---|---|---|
| 5,765,559 | A | 6/1998 | Kim |
| 6,443,156 | B1 | 9/2002 | Niklason |
| 6,526,977 | B1 | 3/2003 | Gobel |
| 6,745,773 | B1 | 6/2004 | Gobel |
| 6,802,317 | B2 | 10/2004 | Gobel |
| 7,121,280 | B2 | 10/2006 | Kyle |
| 7,896,007 | B2 | 3/2011 | Brain |
| 8,196,584 | B2 | 6/2012 | Maguire |
| 8,584,678 | B2 | 11/2013 | Pol |
| 8,636,010 | B2 | 1/2014 | Nelson |
| 9,032,957 | B2 | 5/2015 | Nelson |
| 9,180,268 | B2 | 11/2015 | Wood |
| 9,358,354 | B2 | 6/2016 | Young |
| 9,364,624 | B2 | 6/2016 | Jafari |
| 9,433,737 | B2 | 9/2016 | Graboi |
| 9,474,469 | B2 | 10/2016 | Deutsch |
| 2008/0210243 | A1 | 9/2008 | Clayton |
| 2010/0024827 | A1 | 2/2010 | Tagliavini |
| 2010/0163023 | A1* | 7/2010 | Singh ................ A61M 16/04 128/200.26 |
| 2011/0000484 | A1* | 1/2011 | Melsheimer ........... A61H 9/005 128/202.12 |
| 2012/0279505 | A1 | 11/2012 | Kim |
| 2013/0047992 | A1 | 2/2013 | Kim |
| 2013/0160771 | A1* | 6/2013 | Suijs .................... A61M 16/04 128/207.15 |

* cited by examiner

INTUBATION DEVICE WITH VARIABLE BACKFLOW PRESSURE

FIELD OF THE SUBJECT MATTER

This specification relates to medical devices, and more particularly to intubation devices and methods.

BACKGROUND

Background on Intubation Devices:

Intubation devices provide passage to gases, to mechanically ventilate the lungs, and to apply anesthetic agents and certain medications. Typically, they are connected through a catheter mount to machines that pump and control the flow of such gases (herein, the term "Ventilator" refers to such machines).

Intubation devices include endotracheal tubes, tracheostomy tubes, laryngeal mask airways, endobronchial tubes, and supraglottic tubes. In this specification, the term "Tube" refers to the conduit that such devices use for the ventilation gases, while the term "Duct" refers to significantly smaller diameter conduits, which are typically used for purposes such as inflating cuffs, and suctioning fluids.

To control the type and amount of substances flowing into a patient's lungs, it is necessary to seal the space around the tube, so that gases are forced to flow in and out of the lungs exclusively through the tube's ventilation lumen. In addition, the seal prevents contaminated fluids from entering the lungs. In this specification, the term "Contaminated Fluids" (CFs) refers to fluids such as nasopharyngeal secretions, esophageal reflux, blood, and debris.

Endotracheal Tubes (ETTs) usually have a seal consisting of an inflatable cuff (herein, "Tracheal Cuff") that surrounds the distal portion of the tube. After an ETT is placed in the trachea, the cuff is inflated, so it fills the tracheal passage around the tube, and thus provides an annular seal. Cuffs are soft and collapsible, to allow insertion of the device without damaging the vocal chords, or the tracheal mucosa. The cuffs are inflated through a small duct, which connects to a small-diameter lumen inside of the tube's wall. This lumen, in turn, connects to the cuff through an opening in the tube's wall.

Laryngeal Mask Airways (LMAs) do dot provide as good a seal as ETTs, but are easier to place. LMAs have an inflatable seal that consists of an oval mask, with an attached peripheral ring. When the peripheral ring is inflated, it causes the mask to form a seal against the glottis. Unlike ETTs, LMAs do not risk damaging the vocal chords, or the trachea, as their tubes does not enter the trachea. Instead, LMAs have a tube that terminates at an opening of the mask. This opening allows the passage of ventilation gases, while the mask confines them to the tube. Herein, "Inflating the Seal", when referring to LMAs, means inflating the corresponding ring.

Blind-Insertion Airways (BIAs) have an oropharyngeal cuff, and a smaller esophageal cuff. Gases flow to the lungs through a lateral opening in the tube, located between the oropharyngeal cuff and the esophageal cuff. BIAs with a dual lumen can provide a patent airway even if the esophageal cuff is accidentally placed in the trachea. BIAs are easier to place than ETTs, but do not provide as good a seal. Also, certain medical conditions, or injuries, may prevent using BIAs.

Different devices have been developed to guide the insertion and proper placement of intubation devices. For example: (a) markings on the tube wall can be aligned with specific anatomic features, such as the vocal chords, (b) radiographically opaque lines have been attached, to visualize and control the proper insertion depth, and (c) imaging devices facilitate viewing the vocal chords and other anatomical features as the tubes are placed.

Background Related to Leakage:

To avoid accumulation of CFs on the proximal side of the cuff, suctioning devices have been incorporated to ETTs. Suctioning lines connect proximally to a vacuum source, and distally to a small hole in the ETT tube, which is located by the cuff's proximal side. However, under some circumstances, the suctioning holes may be blocked. Consequently, CFs may accumulate. To improve the suctioning, in some devices, the suctioning hole connects to a manifold wrapped flat against the ETT wall, and has multiple suctioning entrances. However, given the geometry of the cuffs and the trachea, not all CFs can be removed. Also, depending on the viscosity of the CFs, suction holes and manifolds can get fully or partially obstructed. In such situations, some CFs can still accumulate, and eventually leak past the cuff.

Given variations in tracheal sizes, cuffs may not be able to expand fully, causing folds in the cuff portions in contact with the trachea. Even micro-channels created by such folds can serve as leak paths that allow CFs to flow past the cuff and eventually reach the lungs. Various sizes, shapes, and materials are used to reduce such leaks. For example, some cuffs are tapered, instead of cylindrical. Cuffs are typically made out of PVC, silicone, or polyurethane. Thinner and more compliant cuffs, typically made out of polyurethane, have been shown to reduce (but not eliminate), leakage of CFs past the cuff. Moreover, thinner cuffs are more delicate, so the risk of rupture is higher.

Background Related to Gas Pressures:

Typically, cuffs are inflated manually. A one-way valve keeps the gases inside the cuff, and the pressure is monitored with a pilot balloon, or with a manometer. Herein, the term "Pressurizer" means a device (or other source) that supplies gas, at a flow rate and pressure appropriate to inflate cuffs, inflate LMA rings, inflate balloons, and in general keep enclosed cavities at a specified pressure. Herein, the terms "Manual Pressurizer", or "Inflator", mean pressurizers consisting of a syringe pump, or equivalent, and operated manually. Herein, the term "Cuff Pressurizer" refers to pressurizers used to inflate cuffs.

Medical practitioners can control and monitor various parameters related to the gases that flow in and out of the lungs of the intubated patient, including the composition of the gases, the flow rate, and various pressures. Two such pressures are the Positive Inspiratory Pressure (PIP), and the Positive End Expiratory Pressure (PEEP).

As the ventilator runs through a breathing cycle, the pressure of the gases on the distal side of the cuff varies between a maximum of PIP and a minimum of PEEP. Since a higher pressure on the distal side of the cuff helps to limit the leakage of CFs past the cuff, the risk of leakage is highest at PEEP.

Herein, all numerical pressure values are expressed in cm of H2O, with 0 cm H2O corresponding to the atmospheric pressure. It is common to set PEEP slightly above atmospheric pressure (e.g., 4-5 cm H2O), to reduce the risk of alveolar damage or collapse. Hypoxemia, and other medical conditions may require higher PEEP values. However, if PEEP is too high, it can cause reduced venous blood flow, undesirable changes in blood chemistry, and other medically unacceptable side effects. Hence, these and other medical reasons limit both the admissible lower and upper values of PEEP, and determine their optimal values for each patient and pathology.

In general, higher cuff pressures reduce capillary flow in the tracheal mucosa. With a pressure of under 20 cm H2O the tracheal mucosa is normally perfused, but at 30 cm H2O it is already slightly blanched, and at 40 cm H2O arterioles are occluded. Excessive cuff pressure, depending on its duration and magnitude, can cause damage to the tracheal tissue, including ischemia, necrosis, and ulceration. Cuff inflation typically targets pressures of approximately 20 to 30 cm H2O, as a suitable compromise between the impact of the cuff on the tracheal mucosa, and how well it seals the space surrounding the tube.

Seepage of CFs between the cuff and the trachea could be avoided altogether if there were no constraints on how much PEEP and the cuff pressure can be raised. However, these pressures are constrained, because of the reasons explained above. Therefore, simply raising PEEP or the cuff pressure to obtain an assured seal, are not viable options.

Unmet Needs Related to Intubation:

In conclusion, in spite of proper use of medical protocols and techniques, and of the aforementioned improvements to intubation devices, small amounts of CFs still can leak past the cuffs. Furthermore, some of these CFs can get aerosolized, and thus carry bacteria deeply into the lungs. Serious infections associated with the use of intubation are common, particularly with longer intubation times. Such infections frequently lead to Ventilator Associated Pneumonia (VAP), and increase morbidity and mortality rates. Thus, there remains a considerable need for improved intubation devices and methods.

BRIEF SUMMARY OF THE SUBJECT MATTER

The present inventive material is directed to devices, systems, and methods for intubation, wherein the leakage of secretions and other fluids into the lungs is reduced or eliminated. The intubation devices comprise multiple seals, and means to advantageously set the pressure difference between the proximal and distal sides of the most proximal seal, independently of PEEP.

Some embodiments of the intubation device comprise:
a. an endotracheal tube with a proximal and a distal inflatable seal;
b. means to inflate the seals;
c. an annular chamber enclosed by the two seals, the tube, and a patient's surrounding anatomical features (herein, "Chamber"); and
d. means to pressurize the chamber.

A method of using this embodiment comprises setting independently (a) the ventilation parameters for the gases that flow into the tube, (b) the pressure at which the cuffs are inflated, and (c) the pressure for the chamber.

PEEP is set based on medical needs, such as alveolar function, ventilation requirements, and blood chemistry. The chamber pressure is set at a value lower than that of the lowest cuff pressure, but higher than PEEP. When the chamber pressure is raised, the pressure difference between the proximal and distal sides of the proximal cuff increases, independently of PEEP.

As an example, when PEEP is set to 5 cm H2O, and both cuffs are inflated to a pressure of 25 cm H2O, then a chamber pressure of 15 cm H2O is operational. The 15 cm H2O of backwards pressure across the sides of the proximal cuff compares favorably to the 5 cm H2O of PEEP, and reduces the risk of leaks, infections, and VAP.

Other embodiments of the inventive material further comprise a processor, sensors, and additional sources of pressure-regulated gas. Variants thereof comprise variable chamber pressures, under the control of a processor. These pressure variations are typically cyclical, and clear contaminated fluids accumulated between the proximal seal and the trachea, and within microchannels in the proximal cuff, by pushing them backwards.

Various objects, features, aspects, and advantages of the present invention will become more apparent from the following detailed description of embodiments of the invention, along with the accompanying drawing.

BRIEF DESCRIPTION OF THE FIGURES

The figures described herein and the embodiments to which they refer are to be considered illustrative, and not restrictive.

DETAILED DESCRIPTION OF THE SUBJECT MATTER

Leakage of CFs to the lungs of intubated patients can cause VAP. The inventive material herein relates to reducing or eliminating the leakage of CFs past intubation devices. This is accomplished through different structures that generally comprise multiple seals, arranged in ways that result in a reverse pressure gradient across the most proximal seal, without interfering with the ventilation pressure parameters.

(1) Backflow Pressure in Intubation Devices with Two Tracheal Cuffs (1.1) Structure When the same member appears in multiple figures, the same reference number is used. The first digit of the reference is always the figure number in which such member is first depicted.

Herein, the term "Continuous-Pressurizer" means a type of pressurizer whose output pressure is regulated continuously, and stays at a desired value (independently of leaks, temperature variations, and other factors). Herein, the term "Chamber Continuous-Pressurizer" refers to a continuous-pressurizer used to pressurize a chamber.

Figure 1:
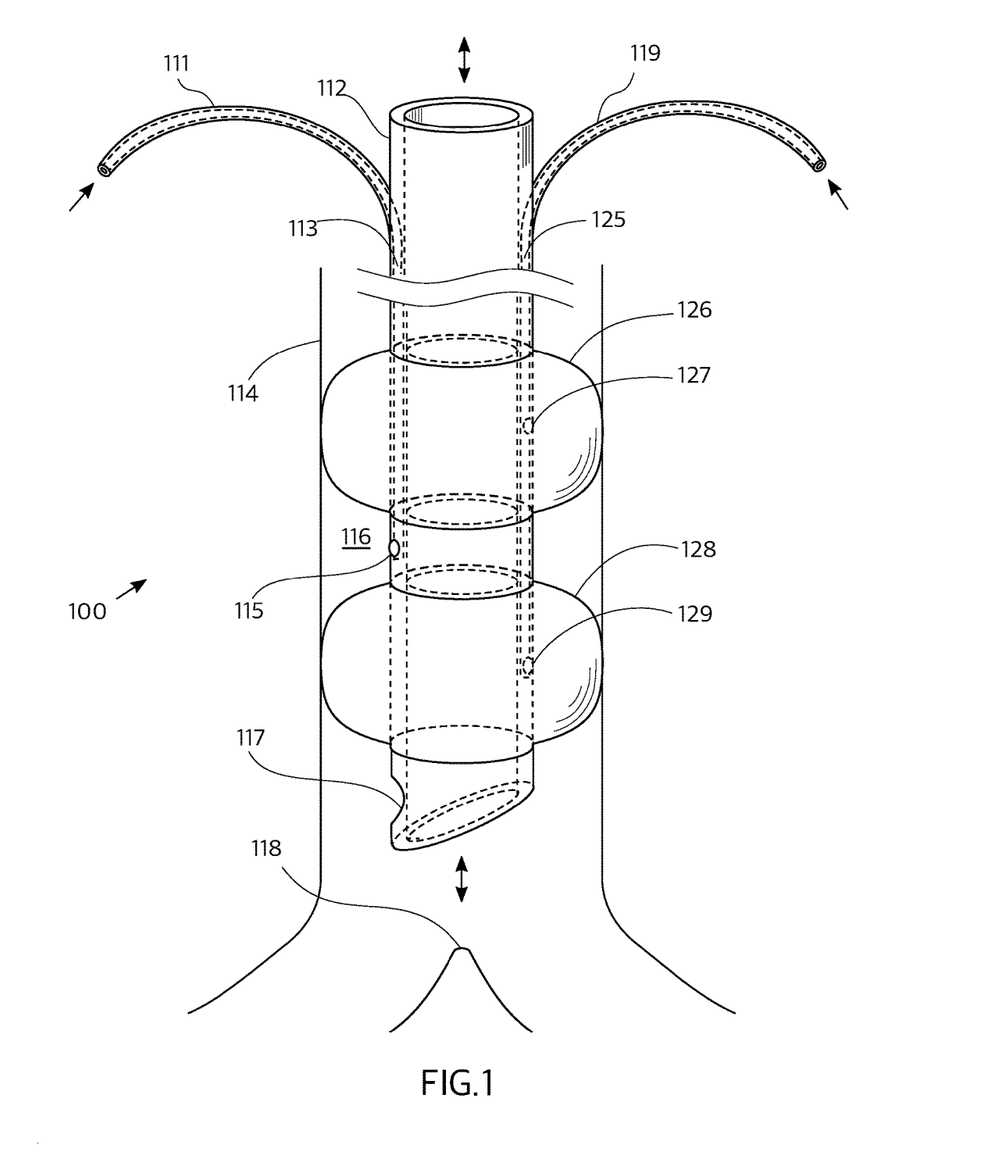
FIG. 1: shows a schematic, external and internal view, of an embodiment of an intubation device with two identical cuffs, a chamber, and an inflator.
Figure 3:
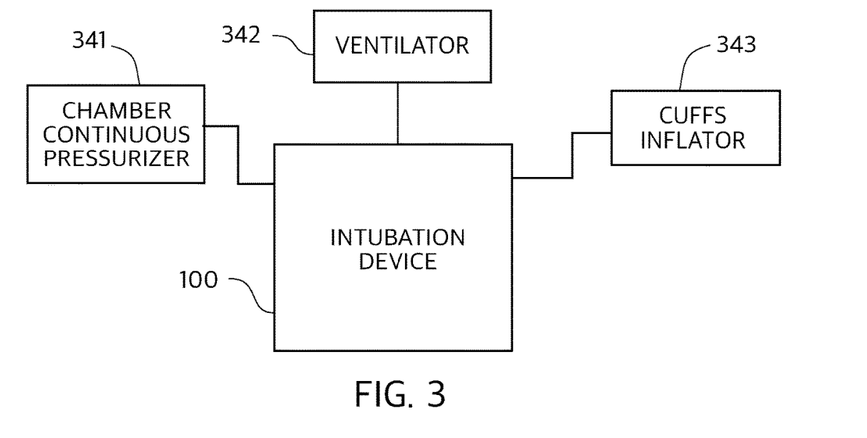
FIG. 3: shows a block diagram of the device depicted in FIG. 1, a pressurizer, an inflator, and a ventilator.

Following the block diagram in FIG. 3, a first preferred embodiment of the inventive material comprises an intubation device 100 (whose internal structure is shown in FIG. 1, and is described next), a chamber continuous-pressurizer 341, and a cuffs inflator 343.

Following the schematic illustration in FIG. 1, the intubation device 100 comprises: a tube 112 with a Murphy's Eye 117 at its distal end; a proximal, inflatable cuff 126 and a distal, inflatable cuff 128, both attached to the tube 112; an annular chamber 116, which is bounded proximally by the cuff 126, distally by the cuff 128, internally by the tube 112, and externally by a patient's trachea 114; a chamber duct 111, whose distal end is connected to the proximal end of a chamber lumen 113; a cuffs duct 119; and a cuffs lumen 125. Furthermore, the distal end of the cuffs duct 119 is connected to the proximal end of the cuffs lumen 125; and the chamber 116 connects to the distal end of the chamber lumen 113, through a first opening 115 in the wall of the tube; and the cuffs 126 and 128 are both connected to the cuff lumen 125, through a second opening 127, and a third opening 129, respectively.

In this embodiment, following FIG. 3 and FIG. 1, the chamber continuous-pressurizer 341, a ventilator 342, and the cuffs inflator 343, are fluidly coupled, respectively, to the following members of the intubation device 100: the chamber duct 111, the tube 112, and the cuffs duct 119.

Other embodiments comprise at least one of the following functionally equivalent variations: (a) the chamber lumen is replaced with a second chamber duct, and (b) the cuffs lumen is replaced with a second cuffs duct.

(1.2) Design and Materials

The tube is made out of one of: PVC, stainless steel, and other biocompatible materials. The diameter and length is based on tracheal size, so different sizes are used for different patients, as is done with standard ETTs (herein, the term "Standard" is used to refer to current devices and practices, and does not imply basic, or minimal devices or practices). The cuffs shapes include cylindrical and tapered, as in standard ETTs. The cuffs are made out of one of: PVC, polyurethane, silicone, and other biocompatible materials. The cuffs diameter is based on tracheal size, cuff shape, cuff material, and inflation pressure, as is done with standard ETTs.

To cover appropriately different patients, tubes and cuffs are made within a range of sizes (similar to those of standard ETTs, except for the length of each cuff). Following FIG. 1, since this embodiment uses two cuffs, which are placed in between the vocal chords (not shown) and the carina 118, and there is a need for some margin of error when placing the device in the trachea 114, each of the cuffs in this embodiment cannot be as long as those used in standard ETTs. Preferably they have a length of approximately 15 mm to 45 mm.

While the proximal cuff 126 blocks the CFs, the distal cuff 128 essentially helps keep the pressure in chamber 116. Hence, leaks past the proximal cuff are more problematic than past the distal cuff. Consequently, each cuff can have a different length, and preferred ratios between the proximal and distal cuff lengths are within a range of approximately 3:1 to 3:2. However, other cuff lengths and ratios are operational, and are contemplated.

Herein, "Essentially Contiguous" means touching, or at a minimal distance (e.g., compatible with manufacturing constraints). Following FIG. 1 or FIG. 2, in order to fit the device in between the vocal chords and the carina 118, it is advantageous to minimize the space in between the cuffs. Towards that end, it is possible to attach the cuffs to the tube with their proximal end folding in the distal direction, under the cuff, and the distal end folding in the proximal direction, also under the cuff (herein, "Folding Internally").

To place the cuffs along the tube more compactly, some embodiments include at least one aspect in the following list: (a) one or both cuffs fold internally, on one or both ends; (b) proximal cuff 126 is essentially contiguous to chamber opening 115; (c) chamber opening 115 is essentially contiguous to distal cuff 128; and (d) distal cuff 128 is essentially contiguous to Murphy's Eye 117 (herein, "Disposed with a Compact Layout" refers to such disposition of members of intubation devices).

(1.3) Operation and Advantages

Following FIG. 1, using this embodiment comprises the following steps (herein, "Setting up the Intubation Device"): (a) tube 112 is properly placed in the patient's trachea 114, using visual, imaging, or radiographic techniques; (b) the cuffs 126 and 128 are properly inflated through the duct 119, thereby sealing the tracheal passage around the cuffs; (c) the chamber 116 is pressurized through the duct 111; and (d) ventilation is provided to the patient through the tube 112. The continuous-pressurizer replenishes automatically whatever gas may leak out of the chamber 116, to keep its pressure substantially constant. The arrows indicate the normal direction in which the gases flow.

Herein, the term "Backflow Pressure" (BFP) means the difference between the pressure in the chamber 116, and the pressure of a column of CFs (PCF) on the proximal side of the proximal the cuff 126. The PCF will depend on multiple factors, such as the patient's pathology, the procedure, and the suctioning of CFs. For the numerical examples a range of approximately 0 to 3 cm H2O is used for the PCF (values outside this range do not change the essence of the examples).

Increasing BFP reduces leakage of CFs across the proximal cuff 126. However, the pressure in the chamber 116 can't be set higher than the pressure inside the cuffs 126 and 128, because otherwise the cuffs would collapse inwardly. Hence, the pressure setting of the cuffs defines an upper limit pressure for the chamber 116. The pressure in the chamber 116 is actually set at a value somewhat lower than the aforementioned upper limit. Herein, the term "Pressure Safety Margin" (PSM) is used for the difference between the upper limit pressure, and the actual pressure in the chamber 116. Preferably it ranges from approximately 2 to 15 cm H2O (but other values are operational too).

The following example uses pressure settings that satisfy the constraints and ranges explained above. The cuffs pressure, PEEP, and other flow and pressure parameters of the ventilator are set and monitored per standard medical practices, based on the specific pathology and needs of the patient. As an example: (a) the cuffs are inflated to a pressure of 25 cm H2O, (b) PEEP is set at 5 cm H2O, and (c) PCF is assumed to be 1 cm H2O. With such values, a pressure of 15 cm H2O can be chosen for the chamber 116 (since it satisfies all the constraints). This choice results in a BFP of 14 cm H2O, while PEEP remains unaffected, at 5 cm H2O. In contrast, under the same conditions, a standard ETT would only have a BFP of 4 cm H2O. Naturally, other pressure values can be used.

In standard ETTs, BFP is limited to PEEP minus PCF. In this embodiment, BFP can be set higher than PEEP, by choosing a suitable pressure in the chamber 116. Thus, the risk of leakage of CFs is reduced, independently of PEEP.

(2) Backflow Pressure in Intubation Devices with Pressure-Regulated Cuffs

Multiple possibilities are contemplated in regards to the inflation of the cuffs. For example, in some embodiments, one or both cuffs are inflated with continuous-pressurizers, instead of manual ones. In some embodiments, both cuffs are fluidly coupled to the same pressurizer, while in others each cuff is fluidly coupled to an independent pressurizer. A second preferred embodiment, which is described next, shows the structure and operation of a device in which each cuff is fluidly coupled to an independent continuous-pressurizer.

(2.1) Structure

Figure 2:
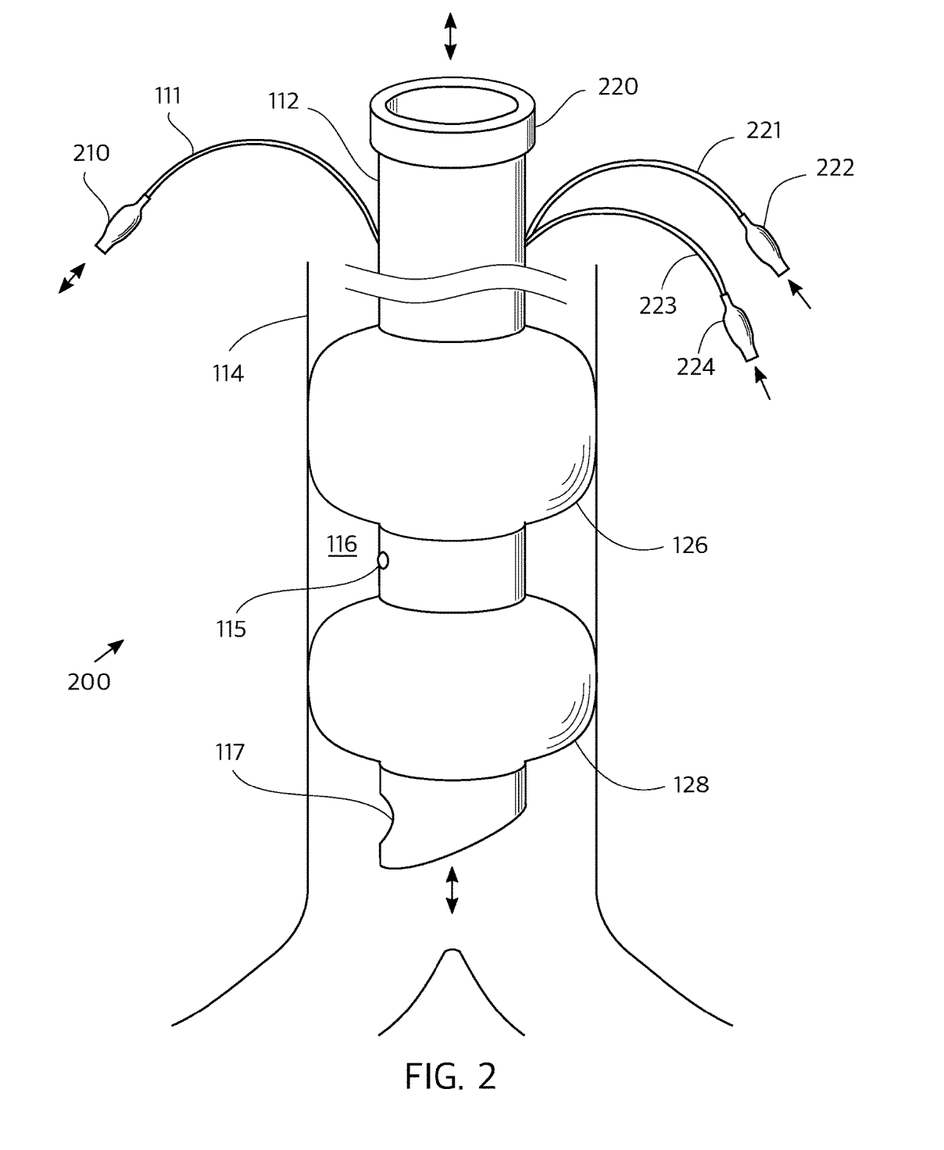
FIG. 2: shows a schematic, external view, of an embodiment of an intubation device with different proximal and distal cuffs, a chamber, and three ducts adapted for receiving gases.
Figure 4:
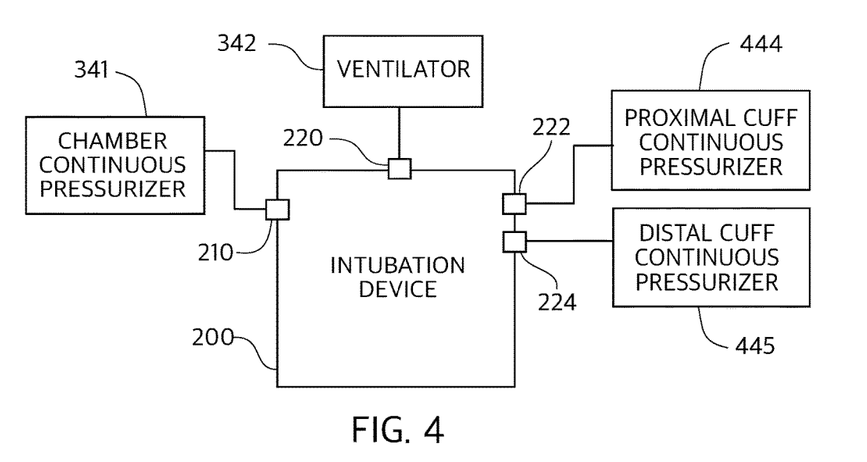
FIG. 4: shows a block diagram of the device depicted in FIG. 2, three pressurizers, and a ventilator.

Following the block diagram in FIG. 4, a second preferred embodiment of the inventive material comprises: an intubation device 200 (whose internal structure is shown in FIG. 2, and is described next), a chamber continuous-pressurizer 341, a proximal cuff continuous-pressurizer 444, and a distal cuff continuous-pressurizer 445.

Herein, "Pneumatic Connector" means connectors suitable for gases under pressure. Following the schematic illustration in FIG. 2, the intubation device 200 comprises: (a) a tube 112 with a pneumatic connector 220 at its proximal end, and a Murphy's Eye 117 at its distal end; (b) a proximal, inflatable cuff 126, attached to the tube 112; (c) a distal, inflatable cuff 128, attached to the tube 112; and (d) an annular chamber 116 bounded proximally by the cuff 126, distally by the cuff 128, internally by the tube 112, and externally by a patient's trachea 114. It further comprises: (e) a chamber duct 111, connected proximally to a pneumatic connector 210; (f) a proximal cuff duct 221, connected proximally to a pneumatic connector 222; (g) a distal cuff duct 223, connected proximally to a pneumatic connector 224; (h) a chamber lumen (not shown) connected proximally to the distal end of the chamber duct 111, and distally to the chamber 116 through an opening 115 in the wall of the tube; (i) a proximal cuff lumen (not shown), which fluidly couples the proximal cuff duct 221, and the proximal cuff 126; and (j) a distal cuff lumen (not shown), which fluidly couples the distal cuff duct 223, and the distal cuff 128.

In this embodiment, following FIG. 4 and FIG. 2 the chamber continuous-pressurizer 341, a ventilator 342, the proximal cuff pressurizer 444, and the distal cuff pressurizer 445, are fluidly coupled, respectively, to the pneumatic connectors 210, 220, 222, and 224.

Other embodiments comprise at least one of the following functionally equivalent variations: (a) the chamber lumen is replaced with a second chamber duct, (b) the proximal cuff lumen is replaced with a second proximal cuff duct, and (c) the distal cuff lumen is replaced with a second distal cuff duct.

(2.2) Operation and Advantages

This embodiment operates as the first preferred embodiment (as described in Section 1), except that (a) the cuffs continuous-pressurizers monitor and regulate the pressures continuously, and thus set and keep the pressure of the cuffs automatically, and more accurately than a manual cuffs inflator; and (b) has independent cuff continuous-pressurizers, which allows the pressure inside each cuff to be different.

As in standard ETTs, setting the pressure of the cuffs accurately is important because if it is too low, the seal is compromised, while if it is too high, the tracheal mucosa is compromised. With this embodiment, it is doubly important, because additional constraints have to be satisfied in regards to the relative pressure of the chamber and the cuffs. Hence, the use of automatic pressure regulation for the cuffs is particularly advantageous.

The two cuffs have a different purpose. The proximal cuff 126 prevents leakage of CF (even minor leaks of CFs past the proximal cuff can endanger patients). The distal cuff 128 prevents leakage of gases from chamber 116 to the lungs, to keep the pressure within the chamber essentially constant. Thus, minor leaks of gases past distal cuff 128 are of no consequence, and the pressure safety margin (PSM) can be smaller for the distal cuff 128 than for the proximal cuff 126.

In an example case, the pressures are set, for the proximal cuff at 25 cm H2O, for the distal cuff at 20 cm H2O, and for the chamber at 15 cm H20. Assuming a PCF of 1 cm H2O, this results in a backflow pressure (BFP) of 14 cm H2O. This is the same BFP as in the example shown for the first preferred embodiment, in Section 1.3, but with the advantage that the pressure in the distal cuff is 20 cm H2O, instead of 25 cm H2O. Naturally, other pressure settings can be chosen, and are contemplated.

(3) Backflow Pressure in Intubation Devices with Supraglottic Proximal Seals (3.1) Structure Variants of the second preferred embodiment (which was depicted in FIG. 2 and FIG. 4, and described in Section 2), use other types of proximal seals. In a third preferred embodiment, an LMA mask is used as a proximal seal (instead of the tracheal cuff 126, depicted in FIG. 2) The LMA mask, which is attached to a tube, seals against a patient's glottis. The tube continues past the LMA mask into the patient's trachea (instead of terminating at the LMA mask, as in standard LMA intubation devices). A distal seal, consisting of a tracheal cuff, is attached to the distal portion of the tube (in the same manner as the distal cuff 128, depicted in FIG. 2). The tube end is tapered, and has a Murphy's Eye, as in standard ETTs.

A proximal seal continuous-pressurizer is fluidly coupled to an LMA ring, which is attached to the LMA mask. A distal seal continuous-pressurizer is fluidly coupled to the tracheal cuff. When the device is placed, and the LMA ring and the cuff are inflated, the LMA mask and the cuff provide proximal and distal bounds to an annular chamber, which is further bounded, internally by the tube, and externally by the patient's surrounding anatomical features (which in this embodiment comprise the trachea, the pharynx, and the epiglottis).

As in the second preferred embodiment, a chamber continuous-pressurizer is fluidly coupled to the chamber, through a pneumatic connector, a first chamber duct, and a chamber lumen inside the tube's wall. The chamber lumen terminates at an opening that connects to the chamber, and is located in the wall of the tube, between the two seals. In other embodiments, the chamber lumen is replaced with a functionally equivalent second chamber duct.

(3.2) Operation and Tradeoffs

The LMA ring pressure, tracheal cuff pressure, and flow and pressure parameters of the ventilator are set and monitored per standard medical practices, based on the specific pathology and needs of the patient. In particular, the LMA ring and the tracheal cuff are inflated to their corresponding, appropriate pressures, by the two independent pressurizers.

Once the intubation device is properly placed, the LMA ring and the tracheal cuff pressures are set. Then the chamber is pressurized, and ventilation is initiated. The LMA mask, and the backflow pressure across the LMA mask, reduce or prevent the passage of CFs past the LMA mask.

Comparing this embodiment with a standard LMA intubation device, it has (a) an advantage: the backflow pressure across the LMA mask is higher than PEEP, and thus reduces the leakage of CFs past the LMA mask, and (b) a disadvantage: it is more complex and harder to insert and place than a standard LMA intubation device. Comparing this third embodiment with the second preferred embodiment, it has (a) an advantage: it has a single cuff in the tracheal portion, instead of two, so the tracheal portion can be shorter, and (b) a disadvantage: the risk of leakage of CFs is higher than in embodiments with two tracheal cuffs.

Further embodiments with a similar structure, and with supraglottic seals other than LMAs (such as, for example, oropharyngeal cuffs), are also contemplated, and operate in a similar manner.

(4) Pressure Sources for Cuffs and Chamber

Cuffs in standard ETTs are typically inflated using a syringe. A one-way valve keeps the air inside the cuff, and a pilot balloon is used to check the pressure. However, this results in significant pressure inaccuracy. To set and maintain the pressure of the seals more accurately, continuous-pressurizers can be used instead, but are not required. However, the chamber is not as airtight as cuffs, so it requires a continuous-pressurizer to keep the pressure in the chamber stable.

Continuous-pressurizers can consist of (a) outlets for gas at the required pressure, and (b) self-contained, active devices that take air or other gases and pump them at the required pressure. In either case, they can be used in conjunction with pressure-regulators, to reduce (a) the number sources of gas at different pressures, and (b) the number of active pumps. For example, while the second preferred embodiment uses three pressurizers (FIG. 4), in some embodiments of the inventive material at least one of the continuous-pressurizers is replaced with passive structures (so fewer continuous-pressurizers are required).

(4.1) Pressurizer Gas Source (4.1.1) Structure

Figure 5:
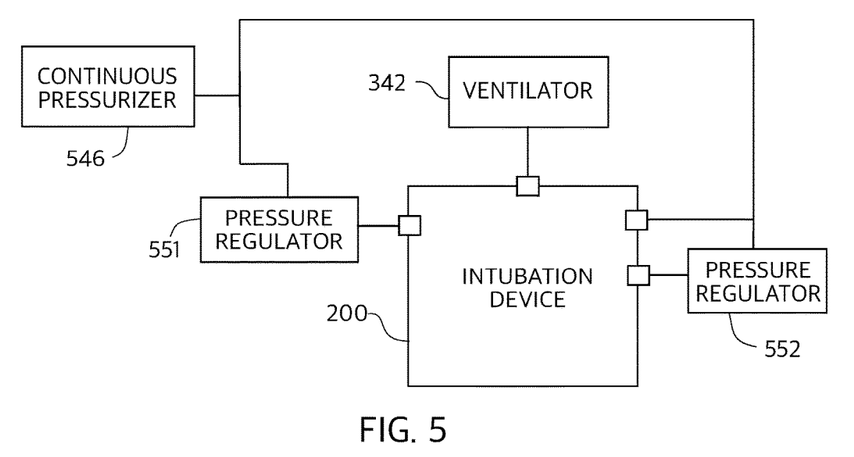
FIG. 5: shows a block diagram of the device depicted in FIG. 2, a pressurizer, two pressure-regulators, and a ventilator.

Following the block diagram in FIG. 5, a fourth preferred embodiment of the inventive material comprises an intubation device 200 (whose internal structure is depicted in FIG. 2, and described in Section 2.1). It further comprises (a) a first pressure-regulator 551, (b) a second pressure-regulator 552, and (c) a single continuous-pressurizer 546.

Furthermore, (d) the continuous-pressurizer 546 is fluidly coupled to the inlets of the two pressure-regulators 551 and 552; (e) the continuous-pressurizer 546 is appropriately sized to supply gas to a chamber and two cuffs; and (f) following FIG. 5 and FIG. 2, the output of the first pressure-regulator 551, a ventilator 342, the pressurizer 342, and the output of the second pressure-regulator 552, are fluidly coupled, respectively, to the following members of the intubation device 200: pneumatic connectors 210, 220, 222, and 224.

(4.1.2) Operation and Advantages

This fourth embodiment operates in the same manner as the second preferred embodiment (Section 2.2), except that the sources of pressure-regulated gas for the distal cuff and for the chamber consist of pressure-regulators, instead of dedicated continuous-pressurizers. Clearly, other configurations that use pressure-regulators to reduce the number of independent continuous-pressurizers are possible. For example, in one variant of this embodiment, both cuffs are inflated to the same pressure, and the pressurizer is fluidly coupled to both cuffs (so pressure-regulator 552 is eliminated).

(4.2) Ventilator Gas Source

Yet another way of taking advantage of one source of gas for multiple purposes is to tap the ventilation gases. Unlike the gas that comes at an essentially stable pressure from a continuous-pressurizer, the pressure of the ventilation gas fluctuates between PEEP and PIP with each breath. Although such pressure range may not be adequate to inflate the cuffs, it is adequate to pressurize the chamber (provided it is appropriately regulated).

Figure 6:
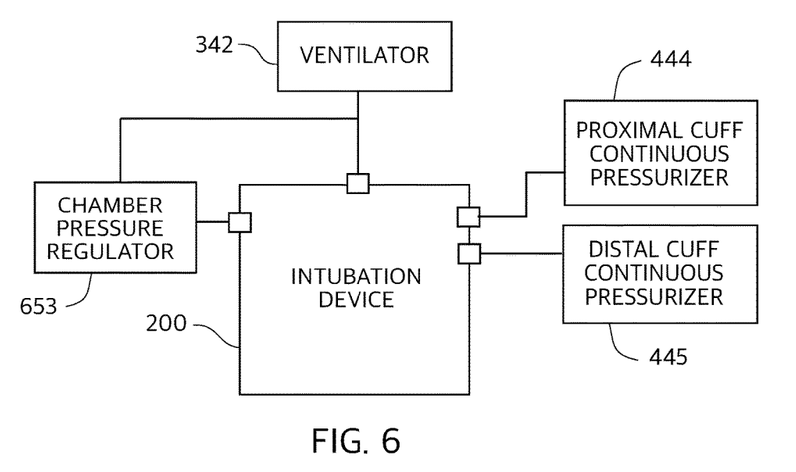
FIG. 6: shows a block diagram of the device depicted in FIG. 2, two pressurizers, a pressure-regulator, and a ventilator.

FIG. 6 shows a block diagram corresponding to a fifth preferred embodiment. It comprises: (a) an intubation device 200 (whose internal structure is shown in FIG. 2, and described in Section 2.1); (b) a chamber pressure-regulator 653; (c) a proximal cuff continuous-pressurizer 444; and (d) a distal cuff continuous-pressurizer 445.

Furthermore, (e) a ventilator 342 is fluidly coupled to the input of the chamber pressure-regulator 653; and following FIG. 6 and FIG. 2, (f) the chamber pressure-regulator 653, and the continuous-pressurizers 444 and 445 are fluidly coupled, respectively, to the following members of the intubation device 200: chamber 116, proximal cuff 126, and distal cuff 128.

In some variants of the fifth embodiment, the pressure-regulator is replaced with a one-way, pressure-reducing valve (herein, "Pressure-Reducer"), which is disposed inside of the tube 112, takes its input directly from the tube 112 ventilation lumen, and outputs to the chamber 116 through the opening 115. A pressure-reducer, while not keeping the pressure in the chamber as stable as a pressure-regulator, is adequate to keep the pressure of the chamber within an operational range. Other pressure-regulators variants would also work, and are contemplated.

(5) Backflow of CFs with Cyclically Variable Backflow Pressure

The embodiments described so far use substantially stable pressures for the seals and for the chamber. However, those pressures can be made to vary in ways that cause a backflow of CFs up the trachea, and away from the seal (herein "Backflow of CFs", or BCF).

To achieve BCF, in some embodiments described next, the pressures in various compartments (the seals and the chamber) are cyclically changed, in a synchronized manner that pushes CFs back. In different embodiments pressure variation rates may range from gradual ramps, as in natural peristalsis, to abrupt, as in natural expectoration. Although cyclical pressure variations are preferred, and are used in the exemplary embodiments described herein, aperiodic pressure variations would work too, and are contemplated. BCF is controlled by a Control System (CS) that receives data from sensors, does certain computations (described next), and controls pressure variations within the chamber and the cuffs.

(5.1) Open-Loop BCF

In open-loop operation the CS runs predetermined sequences of operations, with settings appropriate to cause BCF, without using feedback from sensors.

(5.1.1) Structure

Herein, the term "Information Coupling" refers to a coupling that conveys data and control signals, whether by analog, digital, mechanical, or other means. In the block diagram of FIG. 7, Information couplings are depicted with single lines, while fluid couplings are depicted with two parallel lines. Herein, "Interfaced-Pressurizer" refers to a type of continuous-pressurizer, further having an interface appropriate to be informationally coupled to a CS (which controls the output pressure of the pressurizer).

Figure 7:
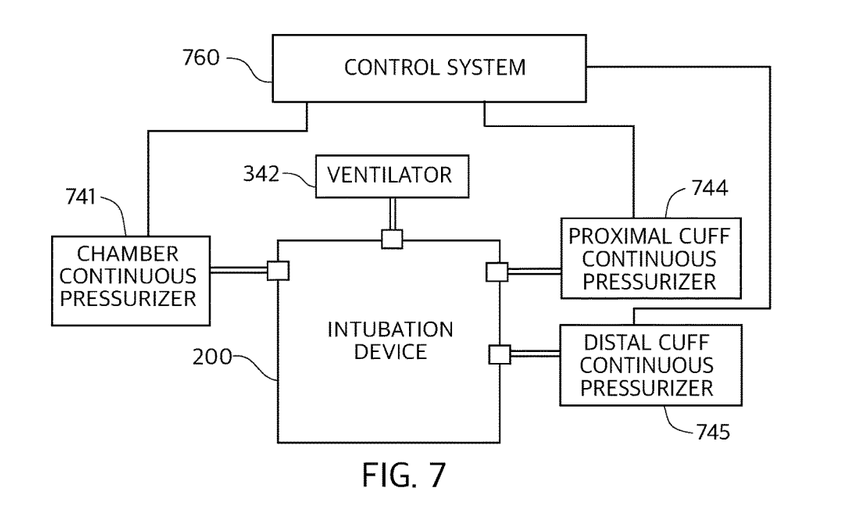
FIG. 7: shows a block diagram of the device depicted in FIG. 2, three pressurizers, a control system, and a ventilator.

Following FIG. 7 and FIG. 2, a sixth preferred embodiment of the inventive material comprises: (a) an intubation device 200 (whose internal structure is depicted in FIG. 2, and described in Section 2.1); (b) a chamber interfaced-pressurizer 741; (c) a proximal cuff interfaced-pressurizer 744; (d) a distal cuff interfaced-pressurizer 745; and (d) a control system 760. Furthermore, (e) a ventilator 742, and the interfaced-pressurizers 741, 744, and 745 are fluidly coupled, respectively, to the following members of the intubation device 200: pneumatic connectors 220, 210, 222, and 224.

The CS 760 comprises a processor, a computer memory, a computer media, and at least one program stored in the computer media. The CS 760 further comprises a UI (through which it is possible to select, for example, programs, modes, operating parameters, and run times), and a timer (or other means for the processor to determine the passage of time, such as the processor's clock). The CS 760 is informationally coupled to, and determines the pressure of, at least one of the interfaced-pressurizers (preferably the one pressurizing the chamber). In this exemplary embodiment it is coupled to all three pressurizers.

(5.1.2) Operation

Operation comprises the capabilities of the second preferred embodiment (Section 2), and further provides automated backflow of CFs. BCF operation comprises: (a) upon receiving commands from the UI, or input from the timer, the CS loads a first program from the computer media into the computer memory (if it was not already loaded into the memory), and starts (or continues) its execution; (b) the first program uses the data it receives from the UI, and time information from the timer, to makes calculations; and (c) the CS, based on the results of those calculations, sends appropriate control signals and data to the interfaced-pressurizers, through information couplings, to set their output pressures.

The pressure changes are coordinated by the first program, and cause pulses that push back any CFs that may have accumulated between the trachea and the proximal cuff, and within microchannels in the proximal cuff.

In some embodiments different modes of operation are programmed as different options within a program, while in other embodiments such options are implemented as separate, smaller programs. Herein the term "Pressure Waveform" (PW) refers to a pressure as a function of time (e.g., a rectangular, trapezoidal, saw-tooth, sinusoidal, or other waveform). Parameters that affect the behavior of the programs comprise: how frequently it runs, the frequency of the PWs, the shape of the PWs, the amplitude of the PWs, and the relative phases between the PWs for each cuff and the chamber. These parameters are set based on the pathology of the patient, the type and amount of secretions, the procedure, the length of intubation time, and other medical aspects. Frequencies preferably range from 0.5 Hz to 100 Hz, and PWs are preferably rectangular or trapezoidal (however, frequencies outside this range, and other PW shapes can be used, and are contemplated).

The amplitude of the PW for the cuffs should be appropriate to generally (but not at all times, as discussed next) conform with the operational upper and lower pressure limits explained in the background, and in sections 1.3 and 2.2. In order to cause BCF, such upper and lower pressure limits are exceeded in this embodiment, by a small margin (preferably less than 4 cm H2O), on a transient basis (preferably less than 1 second).

As an example of operation, transiently (herein, preferably for less than a second), at the same time that the pressure in the proximal cuff decreases, the pressure in the distal cuff increases above normal cuff pressures, and the pressure in the chamber increases above the pressure of the proximal cuff (herein, "Chamber Excess Pressure"). The chamber excess pressure (CEP) is such that the repeated pulses of CEP cause the CFs to flow back up, but is not high enough that they result in a separation of the proximal cuff from the trachea that would enable CFs to flow down, past the cuff. Herein, the term "appropriate chamber excess pressures" is used to refer to such CEPs, and the preferred values are smaller than 4 cm H2O. The appropriate CEP in specific embodiments depends on multiple factors, comprising: (a) the PW frequency, (b) the duty factor (for rectangular and trapezoidal PWs), (c) cuff shape (e.g., cylindrical or tapered), size, and material, and (d) the viscosity of the CFs.

Figure 8:
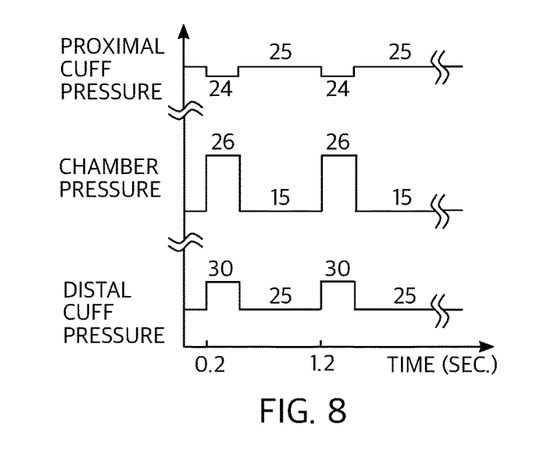
FIG. 8: shows pressure waveforms related to an open-loop mode of operation of the device depicted in FIG. 7

FIG. 8 shows a graph of the PWs in an operation example of this embodiment. The graph shows pressures (a) in the initial state, and (b) then, through two cycles (the pressures values are noted on the waveforms, and are in cm of H2O).

As an example, upon a command issued by the UI, the processor runs for 10 minutes, causing PWs that are synchronous, rectangular (with a 30% duty cycle), at 1 Hz. This example assumes that initially (a) both cuffs have a pressure of 25 cm H2O, and (b) the chamber's pressure is 15 cm H2O. Starting at 0.2 sec., every 1 sec., and for a duration of 0.3 sec.: (a) the PW of the proximal cuff is reduced to 24 cm H2O, (b) the PW of the distal cuff is raised to 30 cm H2O, and (c) the PW of the chamber is raised to 26 cm H2O. The duration, duty cycle, pressures, frequencies, and PW shapes above are just exemplary, and other values and shapes are contemplated too.

(5.2) Closed-Loop BCF

While in open-loop embodiments the PWs are fixed and the CS does not use sensed data, closed-loop embodiments use sensed data to adjust the PWs. Closed-loop embodiments further comprise at least one sensor, informationally coupled to a CS. Such sensors, which can be either stand-alone, or be part of a pressurizer, provide feedback to the processor. Based on such feedback, programs running in the processor can control and vary the pressure settings appropriately. With a closed-feedback loop, the BCF can proceed with the lowest possible appropriate CEP.

(5.2.1) Structure

A seventh preferred embodiment is a variant of the sixth preferred embodiment (which was described in Section 5.1), and further provides BCF with a closed feedback loop. Following FIG. 7 and FIG. 2, this seventh preferred embodiment comprises the structure of the sixth preferred embodiment, and further comprises a flow sensor (not shown) that (a) senses the gas outflow rate from the pressurizer 741 (into the chamber 116), and (b) sends such sensed data to the CS 760, to which the flow sensor is informationally coupled. Many variations are possible, and are contemplated.

(5.2.2) Operation

Operation of the seventh preferred embodiment comprises the capabilities of the sixth preferred embodiment (explained in Section 5.1.2), and further provides automated backflow of CFs using a closed feedback loop. The operation of this embodiment comprises: (a) providing the seventh preferred embodiment (Section 5.2.1), (b) selecting a second program through the UI, and (c) the CS 760 loading and executing the second program (whose operation is described next). This causes CEP pulses, which in turn cause BCF.

The CS 760 receives sensed data, which is used by the second program to adjust said CEP appropriately, as time elapses. In this embodiment, the sensed data originates in the flow sensor, and CEP results from (a) reducing the pressure of the proximal cuff 126 to a constant value, and (b) varying the pressure in chamber 116 at the same time. An operation example, including exemplary steps and values, is described next.

This example assumes that initially, (a) both cuffs 126 and 128 have a pressure of 25 cm H2O, (b) that the chamber has a pressure of 15 cm H2O, and (c) that a desired run time of 40 seconds has been entered in the UI. Initially, the CS 760 raises the pressure of the distal cuff 128 to 30 cm H2O, and reduces the pressure of the proximal cuff 126 to 20 cm H2O. Then, the second program increases the pressure of the chamber 116 by one pressure step per time increment (until meeting conditions described next). When the flow sensor indicates a gas outflow rate exceeding a certain threshold, the CS resets the pressure of the chamber 116 to its original value of 15 cm H2O. The reduced pressure in the chamber causes the outflow from chamber 116 to stop, and the loop restarts (provided that the time elapsed since the second program started has not reached yet the desired operation time). Finally the second program resets the chamber and cuff pressures to their original values.

Preferred time increments are of approximately 0.02 sec to 0.2 sec, and preferred pressure steps are of approximately 0.05 cm H2O to 0.5 cm H2O, but values outside this range are operational, and are contemplated too. The steps in the second program are shown in a flowchart, in FIG. 9, and for the example values above, comprise:
  a. first, "Set Up Cuffs" (saving the original pressure values of the chamber and of each cuff, and afterwards (1) reducing the pressure in the proximal cuff 126 to 20 cm H2O, and (2) increasing the pressure in the distal cuff 128 to 30 cm H20);
  b. then, "Step Chamber Pressure Up" (increasing the pressure in the chamber 116 by a pressure step);
  c. then, "Time" (when the elapsed time since the second program started is less than 40 sec., proceeding to step "d", and otherwise proceeding to step "g");
  d. then, querying the flow sensor;
  e. then, "Flow" (when the sensed outflow is below a predetermined threshold, proceeding to step "b", and otherwise proceeding to step "f");
  f. then, resetting the pressure in chamber 116 to 15 cm H20, and afterwards proceeding to step "b";
  g. then, "Reset All" (using the saved values to reset the cuffs and the chamber to their original pressures); and
  h. then, finally, "End" (terminating the second program).

Figure 9:
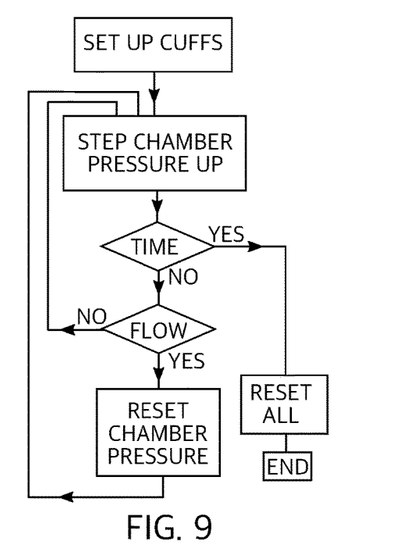
FIG. 9: shows a flowchart related to a closed-loop mode of operation of the device depicted in FIG. 7

Setting appropriate thresholds for the sensed flows and pressures, results in proximal cuff 126 to pulse, as CFs pulse back up. Preferred values for the aforementioned flow threshold are approximately in the range of 2% to 10% of the chamber volume per cycle, but values outside this range are operational, and are contemplated too.

Programs can run just once, as in the example above, or automatically, for example, for 30 seconds, every 20 minutes, to keep the layer between cuff 126 and the trachea 114, as well as any microchannels in the proximal cuff 126, clear of CFs. Naturally, other times and pressures can be specified through the UI.

In this embodiment, the CS uses a simple feedback mechanism, senses outflows from the chamber, and applies steps changes to the controlled pressures. However in other variants, the CS uses pressure flow sensor information to control the feedback loop. Yet other embodiments use non-step changes for the PWs (such as continuous changes), as well as other feedback mechanisms (such as Integral, derivative, adaptive, and other well-known, more advanced feedback systems). Still other embodiments produce a CEP by lowering the pressure in the proximal cuff, while keeping the chamber pressure constant. Many other variations are possible, and are contemplated.

The sixth and seventh preferred embodiments, and the methods described in Section 5, take advantage of the ability to create a backflow pressure (BP) across the proximal cuff (as was explained in Sections 1 and 2), and extend it further to cause the pressures in different compartments to vary in time. The embodiments and methods described in this section (using either open or closed feedback loops) cause BCF through cyclically variable chamber and cuff pressures. Many other variations will be apparent to those familiar with the design of automatic control systems and of intubation devices, and are also contemplated.

(6) Veterinary and Other Uses

The present subject matter is directed, but in no way limited to, devices and methods for the mechanical ventilation and the introduction of other gases to a human patient's lungs. Embodiments comprising systems, kits, and assemblages of materials or components, including at least one of the inventive compositions, can be directed to other purposes. For example, such embodiments may include only a tube with attached seals and connections, while others may also include manual, continuous, or interfaced pressurizers, a ventilator, control systems, and other components configured for a particular use.

Some embodiments are configured for veterinary applications, to treat subjects such as, but not limited to, farm animals, domestic animals, and laboratory animals. Said configuration comprises changes in the preferred numerical values and ranges given herein for human patients, to those appropriate for the specific animal.

An additional and independent purpose and benefit of the pressure pulsations described in Section 5, particularly when the intubation period is long, is to massage the tracheal mucosa, activating capillary flow.

(7) General
  a. In this specification, the term "or" means "Inclusive OR", except when preceded by "either", in which case it means "Exclusive OR". For example, "A, B, or C" is equivalent to "one or more out of A, B, and C". Instead, "either A or B" means "only one out of A and B".
  b. Subsection headings and numbering are provided for convenient reference only, and do not otherwise modify or restrict in any way the interpretation of this specification, or the scope of the inventive material.
  c. Herein, upper and lower case versions of a given word have the same meaning.
  d. All ranges set forth herein are deemed to be inclusive of the endpoints.
  e. All references herein are incorporated to the specification by reference, in their entirety. The publications discussed herein are provided solely for their disclosure prior to the filing date of the present application. Nothing herein is to be construed as an admission that the present invention is not entitled to antedate such publication by virtue of prior invention. Furthermore, where a definition or use of a term that is incorporated by reference herein is inconsistent or contrary to a definition of that term provided herein, the definition of that term provided herein supersedes the one in the reference.
  f. In this specification, the terms "comprises" and "comprising" should be interpreted as referring to elements, components, or steps in a non-limiting manner, indicating that the referenced elements, components, or steps are present, and may be utilized, or combined with other elements, components, or steps that are not expressly referenced. In general, the terms used herein are intended as open terms (e.g., the term "includes"

should be interpreted as "includes but is not limited to," and the term "comprises" should be interpreted as "comprises at least".)

g. Herein, specific structures, methods, and advantages of intubation devices and systems have been disclosed. It should be apparent, however, to those skilled in the art that many more modifications besides those already described are possible without departing from the inventive concepts herein. In interpreting the disclosure, all terms should be interpreted in the broadest possible manner consistent with the context. The above description contains numerical values and many other specificities that should not be construed as limitations on the scope of the inventions, but rather as examples of embodiments of the inventive material. Accordingly, the scope of the inventions should not be determined by the described embodiments or by any numerical values therein, but by the claims and their equivalents.

What is claimed is:

1. An intubation device, comprising:
I. a tracheal tube, which has a wall, and a ventilation lumen;
II. an inflatable, proximal seal, attached to the tube, which has a proximal and a distal side;
III. an inflatable, distal seal, attached to the tube, which has a proximal and a distal side, and consists of a tracheal cuff;
IV. a chamber, which is an annular cavity that, when the device is properly placed and the seals are inflated, is configured to be enclosed
   a. proximally by the distal side of the proximal seal,
   b. distally by the proximal side of the distal seal,
   c. internally by the wall of the tracheal tube, and
   d. externally by a patient's surrounding anatomical features;
V. a chamber lumen, located in the wall of the tracheal tube, and whose distal end is fluidly coupled to the chamber through an opening in the wall of the tracheal tube;
VI. a chamber duct, whose distal end is fluidly coupled to the proximal end of the chamber lumen;
VII. a pneumatic connector, which is fluidly coupled to the proximal end of the chamber duct;
VIII. and wherein
   a. the chamber's pressure is lower than the proximal seal's pressure; and
   b. the chamber's pressure is at least 2 cm H2O higher than PEEP.

2. The device of claim 1, wherein the chamber's pressure is set at least 2 cm H2O higher than PEEP, but is otherwise independent of PEEP.

3. The intubation device of claim 1, wherein the proximal seal consists of a seal selected from the group consisting of: (a) a laryngeal mask, (b) an oropharyngeal cuff, (c) a supraglottic cuff, and (d) a tracheal cuff.

4. The intubation device of claim 3, wherein the proximal seal consists of a tracheal cuff.

5. The intubation device of claim 4, wherein the proximal tracheal cuff is axially longer than the distal tracheal cuff.

6. The intubation device of claim 4, wherein the proximal tracheal cuff is at least 10% axially longer than the distal tracheal cuff.

7. The intubation device of claim 4, wherein the pressure of the proximal tracheal cuff is set higher than the pressure of the distal tracheal cuff.

8. The intubation device of claim 4, wherein the pressure of the proximal tracheal cuff is set at least 2 cm H2O higher than the pressure of the distal tracheal cuff.

9. The intubation device of claim 4, wherein the ratio of the axial length of the proximal tracheal cuff to the axial length of the distal tracheal cuffs is one of:
a. 4:3, and
b. 3:2.

10. The intubation device of claim 4, further comprising at least one cuff pressurizer, fluidly coupled to at least one seal.

11. The intubation device of claim 10, wherein
at least one pressurizer consists of an interfaced-pressurizer; and
which further comprises:
   (a) a user interface,
   (b) a computer readable medium,
   (c) at least one program, stored in the computer readable medium,
   (d) a memory, and
   (e) a processor, which is informationally coupled to
      (1) the user interface,
      (2) the computer readable medium,
      (3) the memory, and
      (4) at least one interfaced-pressurizer.

12. The intubation device of claim 11, further comprising:
at least one sensor, informationally coupled to the processor, and sensing data selected from the group consisting of:
   (a) a pressure in the chamber pressurizer output,
   (b) a pressure in the chamber,
   (c) a flow of gas from the chamber pressurizer to the chamber, and
   (d) a combination thereof.

13. A method of clearing contaminated fluids from the trachea, using variable pressures and feedback, comprising:
   (a) providing the intubation device of claim 12;
   (b) receiving commands from the user interface;
   (c) loading a program from the computer readable medium into memory;
   (d) running the program;
   (e) receiving sensed data;
   (f) sending commands to the at least one interfaced-pressurizer, to vary the output pressure of said interfaced-pressurizer repeatedly, wherein said pressures
      (1) vary following waveforms that produce appropriate chamber excess pressures, and
      (2) are controlled by the program, based on at least one of:
         (i) commands received from the user interface,
         (ii) stored data,
         (iii) sensed data, and
         (iv) the program's computations.

14. A method of clearing contaminated fluids from a patient's trachea using variable pressures, the method comprising:
I. providing an intubation device, the intubation device comprising:
   a. a tracheal tube with a wall, and a ventilation lumen;
   b. an inflatable proximal cuff, attached to the tracheal tube, which provides a proximal seal, the proximal seal having a proximal side and a distal side;
   c. an inflatable distal cuff, attached to the tracheal tube, which provides a distal seal having a proximal side and a distal side;
   d. a chamber, comprising an annular cavity such that when the device is properly placed and the proximal cuff and the distal cuff are inflated the chamber is enclosed proximally by the distal side of the proximal cuff, distally by the proximal side of the distal cuff, internally by the wall of the tracheal tube and externally by a patient's surrounding anatomical features;

II. inserting the intubation device into the trachea of a patient;

III. forming the chamber by inflating the proximal cuff and the distal cuff;

IV. pressurizing the chamber to a pressure greater than PEEP but less than the proximal cuff or distal cuff pressures;

V. cyclically varying the chamber pressure and the proximal cuff inflation pressure such that in a first part of the cycle the pressure in the proximal cuff is reduced to less than the chamber pressure and/or the pressure in the chamber is increased to greater than the pressure of the proximal cuff and in a second part of the cycle the pressure in the proximal cuff is increased to greater than the chamber pressure and/or the pressure in the chamber is reduced to less than the pressure in the proximal cuff; and VI. maintaining the distal cuff pressure at a pressure greater than the chamber pressure throughout the cycle.

\* \* \* \* \*